United States Patent
Commereuc et al.

(10) Patent No.: US 6,501,001 B2
(45) Date of Patent: *Dec. 31, 2002

(54) PROCESS FOR SELECTIVE DIMERIZATION OF PROPYLENE PRINCIPALLY INTO BRANCHED DIMERS

(75) Inventors: Dominique Commereuc, Meudon (FR); Dominique Le Pennec, Orgerus (FR); Hélène Olivier-Bourbigou, Rueil Malmaison (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/775,555

(22) Filed: Feb. 5, 2001

(65) Prior Publication Data

US 2001/0018546 A1 Aug. 30, 2001

(30) Foreign Application Priority Data

Feb. 4, 2000 (FR) .............................. 00 01511

(51) Int. Cl.⁷ .............................. C07C 2/26; C07C 2/34

(52) U.S. Cl. ........................ 585/514; 585/513; 585/512; 585/511; 585/521; 585/527; 585/529

(58) Field of Search .................................. 585/511, 512, 585/513, 514, 521, 527, 524

(56) References Cited

U.S. PATENT DOCUMENTS 4,533,651 A * 8/1985 Masters et al. ............. 502/117
5,550,306 A * 8/1996 Chauvin et al. ............ 585/510

FOREIGN PATENT DOCUMENTS

FR 2 710 280 3/1995

* cited by examiner

Primary Examiner—Thuan D. Dang
(74) Attorney, Agent, or Firm—Millen, White, Zelano & Branigan, P.C.

(57) ABSTRACT

In order to carry out selective dimerization of propylene principally into branched dimers, a catalytic composition resulting from at least partly dissolving a nickel compound mixed or complexed with a tertiary phosphine carrying a functional group is used in a medium resulting from mixing at least one quaternary ammonium halide and/or at least one quaternary phosphonium halide, at least one aluminum halide and optionally at least one organometallic aluminum compound.

21 Claims, No Drawings

PROCESS FOR SELECTIVE DIMERIZATION OF PROPYLENE PRINCIPALLY INTO BRANCHED DIMERS

BACKGROUND OF THE INVENTION

1. Field of the Invention

The present invention relates to a process for selective dimerization of propylene principally into branched dimers. More particularly, it relates to a process in which propylene is brought into contact with a catalytic composition resulting from at least partly dissolving a nickel compound mixed or complexed with a tertiary phosphine carrying a functional group in a medium resulting from mixing at least one quaternary ammonium halide and/or at least one quaternary phosphonium halide, at least one aluminum halide and optionally at least one organometallic aluminum compound.

2. Description of the Prior Art

French Patent No. 2,611,700 describes the use of liquids of ionic nature formed from aluminum halides and quaternary ammonium halides as solvents for organometallic nickel complexes to catalyze olefin dimerization. The use of such media, which are not miscible with aliphatic hydrocarbons, in particular with the products from olefin dimerization, enables homogeneous catalysts to be used more effectively. French Patent No. 2,659,871 describes a liquid composition with an ionic nature resulting from bringing quaternary ammonium halides and/or quaternary phosphonium halides into contact with alkylaluminum dihalides and optionally also an aluminum trihalide. That same patent describes the use of such media as solvents for transition metal complexes, in particular nickel complexes containing no nickel-carbon bond, which are transformed into catalysts for olefin oligomerization. In the present text, such media will henceforth be termed "molten salts", as they are liquid at moderate temperatures.

During those studies, it was shown that the most active and most stable nickel catalysts are obtained in "molten salts" constituted by one molar equivalent of an ammonium halide and/or a phosphonium halide with one equivalent and more of an aluminum trihalide, and optionally any quantity of an alkyl aluminum dihalide. That formulation has been shown to be particularly interesting as nickel complexes dissolved in it have high catalytic activity.

Further, it has been shown that under the conditions described in French Patent No. 2,611,700? the "phosphine effect", as described by G. Wilke et al., in Ind. Eng. Chem., 1970, 62, No. 12, p. 34, and in U. K. Patent No. 1,058,680, which reports the influence of substituents carried by the phosphorus atom on the mode of enchainment of propylene molecules during catalytic dimerization by nickel, rapidly disappears over time. That unexplained phenomenon has deleterious consequences since it does not produce the desired selectivities.

French Patent No. 2,710,280 shows that adding an aromatic hydrocarbon to a "molten salt" can overcome this problem and result in catalysts with high activity which are more stable and which have a high selectivity for the most highly branched isomers. However, the aromatic hydrocarbon is continuously extracted in the organic phase constituted by the products, which implies that it must be separated and recycled to the reactor.

SUMMARY OF THE INVENTION

It has now been discovered that the use of a tertiary phosphine carrying a functional group or a nickel complex formed with a tertiary phosphine that is soluble in the "molten salt" results in catalysts for which the selectivity for the most highly branched isomers is high and stable over time and for which the activity is high.

DETAILED DESCRIPTION OF THE INVENTION

The invention provides a process for selective dimerization of propylene into branched dimers in which a catalytic composition comprising at least one nickel compound mixed or complexed with at least one tertiary phosphine carrying a functional group is used, at least partly dissolved in a non aqueous medium with an ionic nature ("molten salt" type medium), resulting from bringing at least one aluminum halide (product B) into contact with at least one quaternary ammonium halide and/or at least one quaternary phosphonium halide (product A), the "molten salt" type medium possibly further comprising at least one organometallic aluminum compound (product C).

Thus the "molten salt" type medium, in which the nickel compound mixed or complexed with at least one tertiary phosphine carrying a functional group or at least one phosphite carrying a function croup is dissolved, is constituted by mixing:

a) at least one quaternary ammonium and/or quaternary phosphonium halide, more particularly a chloride and/or bromide (product A);

b) at least one aluminum halide (product B); and c) optionally, at least one organometallic aluminum compound (product C).

Preferred quaternary ammonium and/or phosphonium halides that can be used within the context of the invention (product A), are:

those with general formula $NR^1R^2R^3R^4X$ (with the exception of $NH_4X$), $PR^1R^2R^3R^4X$, $R^1R^2N=CR^3R^4X$ or $R^1R^2P=CR^3R^4X$, where X represents Cl or Br and $R^1$, $R^2$, $R^3$ and $R^4$, which may be identical or different, each represent hydrogen or a hydrocarbyl residue containing 1 to 12 carbon atoms, for example saturated or unsaturated alkyl, cycloalkyl or aromatic groups, aryl groups or aralkyl groups, containing 1 to 12 carbon atoms, it being understood that preferably, only one of substituents $R^1$, $R^2$, $R^3$ and $R^4$ represents hydrogen;

or one of the following general formulae:

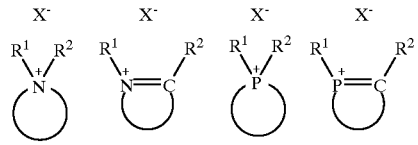

where the nitrogen-containing or phosphorus-containing heterocycles containing 1, 2 or 3 nitrogen and/or phosphorus atoms are constituted by 4 to 10 atoms and X, $R^1$ and $R^2$ are defined as above.

Examples which can be cited are tetrabutylphosphonium chloride, N-butyl pyridinium chloride, ethylpyridinium bromide, 3-butyl- 1-methyl imidazolium chloride, diethylpyrazolium chloride, pyridinium hydrochloride, trimethylphenyl ammonium chloride and 3-ethyl-1-methyl imidazolium chloride. These salts can be used alone or as a mixture.

The aluminum halides used as products B of the invention are essentially aluminum chloride and bromide.

The organometallic aluminum compounds used as optional products C of the invention have general formula $AlR^xX_{3-x}$ in which R is a linear or branched alkyl residue containing 2 to 8 carbon atoms, X is chlorine or bromine and the value of x is 1, 2 or 3. Examples of organometallic aluminum compounds that can be used are isobutylaluminum sesquichloride, ethylaluminum sesquichloride, dichloroisobutyl aluminum, dichloroethyl aluminum and chlorodiethyl aluminum.

The components of the "molten salts" as defined above are generally used in A:B mole ratios of 1:0.5 to 1:3, preferably 1:1 to 1:2; product C is used in a mole ratio of at most 100:1 with product B, preferably 0.005:1 to 10:1. However, the components and their proportions must be such that the mixture is liquid at the temperature at which the nickel compound and the functionalized tertiary phosphine are introduced, although the catalytic dimerization reaction can be carried out at a temperature which is lower than or higher than the fusion temperature of the catalytic composition.

Examples of nickel compounds used in the catalytic compositions of the invention are the chloride, bromide, sulfate, carboxylates (for example the 2-ethylhexanoate), phenates and acetyl acetonate. It is also possible to use organometallic nickel complexes which may or may not contain phosphines. These nickel complexes are used as a mixture with a functionalized tertiary phosphine. It is also possible to use nickel complexes that are already complexed with a tertiary phosphine carrying a function.

The functional phosphines used as a mixture with (or to complex) the nickel compounds of the invention have general formulae $PR'_1R'_2R'_3$ and $R'^1R'_2P$—$R'$—$PR'_1R'_2$, where $R'^1$, $R'_2$ and $R'_3$, which may be identical or different, are alkyl, cycloalkyl, aryl or aralkyl radicals containing 1 to 10 carbon atoms at least one of which carries a functional group such as an amine, a cyclic amine, a nitrogen-containing heterocycle, an ester, an acid, an alcohol, a quaternary ammonium, a quaternary phosphonium, a sulfonium, a sulfonate or a phosphonate and R' is a divalent aliphatic residue containing 1 to 6 carbon atoms.

The functional phosphines can be selected from compounds containing pyridine or imidazole substituents or their quaternized derivatives containing pyridinium or imidazolium substituents that satisfy formulae 1 to 7 defined below.

Examples of functional phosphines carrying a pyridine substituent are 2-dicyclopentyl-phosphinoethyl-4-pyridine with formula (1), 2-dicyclopentylphosphinoethyl-2-pyridine with formula (2), 2-diisobutylphosphinoethyl-4-pyridine with formula (1b), 2-diisopropylphosphinoethyl-4-pyridine with formula (4) and their quaternization derivatives with formula (3), where R is an alkyl group containing 1 to 10 carbon atoms and X is a weakly coordinating anion. Examples of weakly coordinating anions which can be cited are tetrafluoroborate, hexafluorophosphate, tetrachloroaluminate, hexafluoroantimonate, carboxylate anions such as acetate, trifluoroacetate, trifluorosulfonate, and the anions $N(CF_3SO_2)_2^-$ and $C(CF_3SO_2)_3^-$. Examples of quaternization derivatives are 2-dicyclopentylphosphinoethyl-N-ethyl pyridinium tetrafluoroborate with formula (3a), or 2-dicyclopentylphosphinoethyl-N-ethyl pyridinium chloride with formula (3b).

Examples of functional phosphines carrying an imidazole substituent which can be cited are 2-dicyclopentylphosphinoethyl-N-imidazole with formula (5), 2-diisopropylphosphinoethyl-N-imidazole with formula (7), 2-diisobutylphosphinoethyl-N-imidazole with formula (7b) and their quaterization derivatives with formula (6), where R is an alkyl group containing 1 to 10 carbon atoms and X is a weakly coordinating anion (as defined above), such as ²-dicyclopentyl-phosphinoethyl-1-methyl imidazolium tetrafluoroborate with formula (6a).

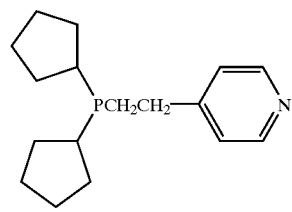

1

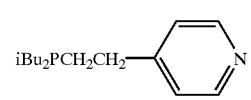

1b

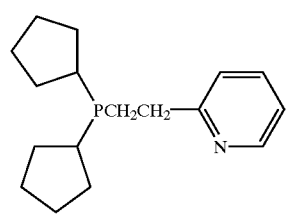

2

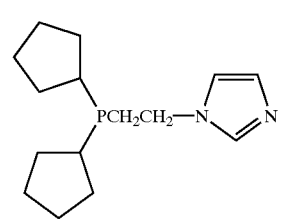

5

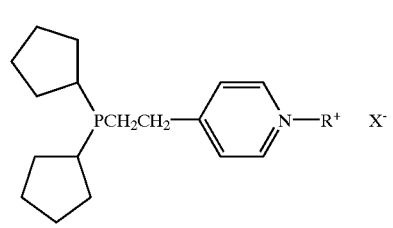

3

X⁻ = BF₄⁻, R = Et    3a

X⁻ = Cl⁻ R = Et    3b

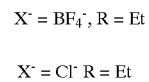

6

X⁻ = BF₄⁻, R = Me    6a

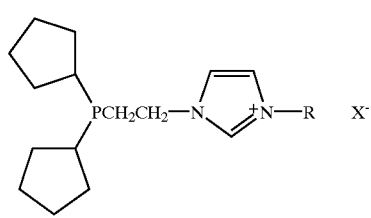

7

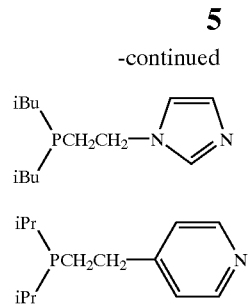

As examples of nickel compounds that can be used to constitute the catalytic compositions of the invention, can be cited the complex complexes [NiCl$_2$, 1.5P(2-dicyclopentylethyl-4-pyridine)]$_2$, [NiCl$_2$, 2P(2-dicyclopentylethyl-N-ethyl pyridinium tetrafluoroborate)], [Ni$_2$Cl$_4$, (2-dicyclopentylphosphinoethyl-N-ethyl pyridinium tetrafluoroborate)$_3$, 1.5 CH$_2$Cl$_2$], NiCl$_2$, 2 pyridine mixed with at least one equivalent of functionalized tertiary phosphine or functionalized phosphite, nickel chloride mixed with at least one equivalent of 2-dicyclopentylphosphinoethyl-4-pyridine, nickel acetate mixed with at least one equivalent of 2-dicyclopentylphosphinoethyl-4-pyridine, nickel (2-ethyl hexanoate) octoate mixed with at least one equivalent of 2-dicyclopentylphosphinoethyl-4-pyridine and 2-dicyclopentylphosphinoethyl-4-pyridine π-allyl nickel chloride.

The compounds forming part of the catalytic composition of the invention can be mixed in any order. The mixture can be produced by simply bringing them into contact followed by agitation until a homogeneous liquid is formed. This mixture can be produced outside the dimerization or oligomerization reactor or, as is preferable, in the reactor.

The propylene which undergoes the selective dimerization of the invention can be used pure or diluted in an alkane, such as those found in C$_3$ cuts from oil refining processes, such as catalytic cracking or steam cracking.

The catalytic propylene dimerization reaction can be carried out in a closed system, in a semi-open system or continuously, with one or more reaction stages. Vigorous agitation must be carried out to ensure good contact between the reactant or reactants and the catalytic mixture. The reaction temperature can be from −40° C. to +70° C., preferably −20° C. to +50° C. It is possible to operate above or below the fusion temperature of the medium, the dispersed solid state not being a limitation to the proper conduct of the reaction. The heat engendered in the reaction can be eliminated using any means known to the skilled person. The pressure can be from atmospheric pressure to 20 MPa, preferably atmospheric pressure to 5 MPa. The reaction products and the reactant or reactants that has/have not reacted are separated from the catalytic system simply by decanting, then fractionation.

The entire disclosure of all applications, patents and publications, cited above and below, and of corresponding French application 00/01511, filed Feb. 4, 2000, are hereby incorporated by reference.

The following examples illustrate the invention without limiting its scope.

EXAMPLE 1
Preparation of ionic solvent 17.5 g (0.1 mole) of 1-butyl-3-methyl imidazolium chloride, 16.3 g (0.122 mole) of sublimed aluminum chloride, 1.6 g (0.0126 mole) of dichloroethyl aluminum was mixed at ambient temperature. A liquid was obtained.

EXAMPLE 2
Preparation of the complex [NiCl$_2$, 1.5 P(2-dicyclopentylethyl-4-pyridine)]$_2$ 2.37 g of NiCl$_2$, 6H$_2$O and 10 ml of absolute methanol were introduced into a Schlenk tube maintained under an argon atmosphere. After the nickel salt had dissolved, 20 ml of pentane was added. The 2 phases were agitated and 5.33 g of tertiary phosphine with formula (1) (20 mmoles) was added. After 2 hours agitation, the red precipitate was filtered. 5.82 g was obtained. Elemental analysis corresponded to the complex with formula [NiCl$_2$, 1.5 P(2-dicyclopentylethyl-4-pyridine)]$_2$ (M=1085 g; 10.7% by weight of Ni).

EXAMPLE 3
Quaternization of pyridine in the complex described in Example 2

3.72 g of the complex described in Example 2 was placed in a Schlenk tube and dichloromethane was added. Then a solution of tetrafluoroborate oxonium in dichloromethane (2.14 g of Et$_3$O$^+$BF$_4^-$) was added dropwise. It was agitated for 4 hours, at the end of which period a red solution was obtained. The solvent was evaporated off and 20 ml of ether was added. The red crystalline solid obtained was filtered off. 4.56 g was obtained. Elemental analysis corresponded to the complex with formula: Ni$_2$C$^4$(P—N$^+$EtBF$_4^-$)$_3$, 1.5 CH$_2$Cl$_2$, where P—N is the ligand with formula (1).

EXAMPLE 4
Propylene dimerization

A glass reactor provided with a temperature sensor, a magnetic bar in the lower stage (20 ml volume) to ensure proper agitation and a double envelope for circulating a cooling liquid was purged of air and moisture and maintained at an atmospheric pressure of 99% pure propylene. 0.03 mmole of the complex prepared in Example 2 (0.06 mmole of Ni) was introduced then the temperature was reduced to 10° C. and 5 ml of the liquid composition prepared above (Example 1) was injected using a syringe, along with 7 ml of heptane. Agitation was commenced and immediately, propylene absorption was observed. When the non-agitated upper stage was full of liquid, the major portion of the hydrocarbon phase had been extracted. The reaction was stopped after 7 hours (5 extractions). At that time, 175 kg of products per gram of Ni had been produced. Analysis of the different fractions showed that they were composed of 77% of dimers. The composition of the dimers, which was practically identical in all of the fractions, was 67% of 2,3-dimethylbutenes, and 29% of methyl pentenes, the remainder being n-hexenes.

EXAMPLE 5
Propylene dimerization

The procedure of Example 4 was carried out, with the exception that the molten salt prepared for this purpose was used, and that 0.05 mmole of nickel (2-ethylhexanoate) octoate and 0.5 mmole of 2-dicyclopentylphosphinoethyl-4-pyridine were introduced. The reaction period was 7 hours 15 minutes, at the end of which 5 fractions had been extracted and 220 kg of products per gram of Ni had been produced. The dimer selectivity was 78%. The selectivity for 2,3-dimethylbutenes was 66% in the first fraction and 63% in the final fraction.

EXAMPLE 6
Propylene dimerization

The procedure of Example 4 was followed, with the exception that the molten salt for this purpose was used, and that 45 mg of the complex prepared in Example 3 was introduced. The reaction period was 7 hours 15 minutes, at the end of which 5 fractions had been extracted and 117 kg of products per gram of Ni had been produced. The dimer selectivity was 74–79%. The selectivity for 2,3-dimethylbutenes was 65% and was constant for the various fractions.

EXAMPLE 7 (COMPARATIVE)
Propylene dimerization

The procedure of Example 4 was followed, with the exception that the molten salt used was that prepared in Example 1, introducing 0.05 mmole of the complex $NiCl_2$, $2P(cyclohexyl)_3$. The reaction was left for 8 hours 30 minutes, at the end of which 10 fractions had been extracted. 137 kg of products per gram of Ni were produced, with a dimer selectivity of 83%. The selectivity for 2,3-dimethylbutenes was 70% in the first fraction; it dropped to 35% in the third and to 10% in the sixth fraction. It was 6% in the tenth fraction.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for selective dimerization of propylene principally into branched dimers comprising dimerizing the propylene in contact with a catalytic composition comprising at least one nickel compound mixed or complexed with at least one tertiary phosphine carrying a funtional group, at least partly dissolved in a non aqueous medium with an ionic nature resulting from bringing at least one aluminum halide (product B) into contact with at least one quaternary ammonium halide and/or at least one quaternary phosphium halide (product A).

2. A process according to claim 1, wherein the nickel compound is a chloride, bromide, sulfate, carboxylate, phenate and acetylacetonate.

3. A process according to claim 1, wherein the tertiary phosphine carrying a functional group has one of the general formulae $PR'_1R'_2R'_3$ or $R'^1R'_2P—R'—PR'_1R'_2$, where $R'_1$, $R'_2$ and $R'_3$, which may be identical or different, are alkyl, cycloalkyl, aryl or aralkyl radicals containing 1 to 10 carbon atoms at least one of which carries a functional group selected from the group consisting of an amine, a cyclic amine, a nitrogen-containing heterocycle, an ester, an acid, an alcohol, a quaternary ammonium, a quaternary phosphonium, a sulfonium, a sulfonate and a phosphonate group and R' is a divalent aliphatic residue containing 1 to 6 carbon atoms.

4. A process according to claim 1, wherein the functional tertiary phosphine is a phosphine containing substituents selected from a group consisting of pyridine, imidazole, quaternization derivatives with pyradinium substituents and quaternization derivatives with imadazolium substituents.

5. A process according to claim 1, wherein the functional tertiary phosphine is selected from the group consisting of 2-dicyclopentylphosphinoethyl-4-pyridine, 2-dicyclopentylphosphinoethyl-2-pyridine, 2-diisobutylphosphinoethyl-4-pyridine, 2-diisopropylphosphinoethyl-4-pyridine, 2-dicyclopentylphosphinoethyl-N-imidazole, 2-diisopropylphosphinoethyl-N-imidazole and 2-diisobutylphosphinoethyl-N-imidazole.

6. A process according to claim 4, wherein the functional tertiary phosphine carries a pyridinium or imidazolium substituent and is a quaternization derivative with one of formulae (3) or (6) where R is an alkyl group containing 1 to 10 carbon atoms and $X^-$ is a weakly coordinating anion, wherein formula (3) is

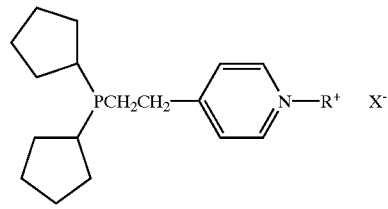

and formula (6) is

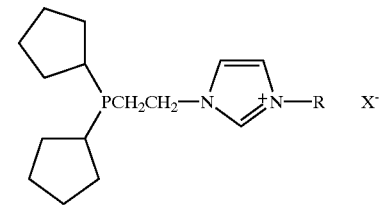

7. A process according to claim 6, wherein the weakly coordinating anion is selected from the group consisting of tetrafluoroborate, hexafluorophosphate, tetrachloroaluminate, hexafluoroantimonate, carboxylate anions, acetate, trifluoroacetate, trifluorosulfonate, $N(CF_3SO_2)_2^-$ and $C(CF_3SO_2)_3^-$ anions.

8. A process according to claim 1, wherein the functional tertiary phosphine carries a pyridinium or imidazolium substituent and is selected from the group consisting of 2-dicyclo-pentylphosphinoethyl-N-ethyl pyridinium tetrafluoroborate, 2-dicyclopentylphosphinoethyl-N-ethyl pyridinium chloride and 2-dicyclopentylphosphinoethyl-1-methyl-imidazolium tetrafluoroborate.

9. A process according to claim 1, characterized in that the nickel compound mixed or complexed with at least one tertiary phosphine carrying a functional group is selected from the following group consisting of: $[NiCl_2, 1.5P(2-dicyclopentylethyl-4-pyridine)]_2$; $[NiCl_2, 2P(2-dicyclopentylethyl-N-ethyl\ pyridinium\ tetrafluoroborate)]$; $[Ni_2Cl_4, (2-dicyclopentylphosphinoethyl-N-ethyl\ pyridinium\ tetrafluoroborate)_3, 1.5\ CH_2Cl_2]$; $NiCl_2$, 2 pyridine mixed with at least one equivalent of functionalized tertiary phosphine; nickel chloride mixed with at least one equivalent of 2-dicyclopentylphosphinoethyl-4-pyridine; nickel acetate mixed with at least one equivalent of 2-dicyclopentylphosphinoethyl-4-pyridine; nickel (2-ethyl hexanoate octoate) mixed with at least one equivalent of 2-dicyclopentyl-phosphinoethyl-4-pyridine; and 2-dicyclopentylphosphinoethyl-4-pyridine π-allyl nickel chloride.

10. A process according to claim 1 characterized in that the quaternary ammonium halide or quaternary phosphonium halide used as product A satisfies one of general formulae: $NR^1R^2R^3R^4X$ with the exception of $NH_4X$, $PR^1R^2R^3R^4X$, $R^1R^2N=CR^3R^4X$ or $R^1R^2P=CR^3R^4X$, where X represents Cl or Br and $R^1$, $R^2$, $R^3$ and $R^4$, which may be identical or different, each represent hydrogen or a hydrocarbyl residue containing 1 to 12 carbon atoms; or one of the following general formulae:

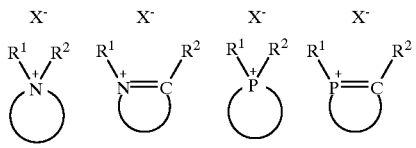

where the nitrogen-containing or phosphorus-containing heterocycles containing 1, 2 or 3 nitrogen and/or phosphorus atoms are constituted by 4 to 10 atoms and X, $R^1$ and $R^2$ are defined as above.

11. A process according to claim 10 characterized in that the quaternary ammonium halide or quaternary phosphonium halide is tetrabutyl phosphonium chloride, N-butyl pyridinium chloride, ethylpyridinium bromide, 3-butyl-1-methyl imidazolium chloride, diethylpyrazolium chloride, pyridinium hydrochloride, trimethylphenylammonium chloride, or 1-ethyl-3-methyl imidazolium chloride.

12. A process according to claim 1 characterized in that the aluminum halide used as product B is aluminum chloride or bromide.

13. A process according to claim 1 characterized in that products A and B are used in an A:B mole ratio of 1:0.5 to 1:3.

14. A process according to claim 1 characterized in that the non-aqueous medium with an ionic nature also comprises a product C, consisting of at least one organometallic aluminum compound.

15. A process according to claim 14 characterized in that the organometallic aluminum compound used as optional product C of the invention has general formula $AlR_xX_{3-x}$ where R is a linear or branched alkyl residue containing 2 to 8 carbon atoms, X is chlorine or bromine and the value of x is 1, 2 or 3.

16. A process according to claim 14 characterized in that product C is isobutylaluminum sesquichloride, ethylaluminum sesquichloride, dichloroisobutylaluminum, dichloroethylaluminum, or chlorodiethylaluminum.

17. A process according claim 14 characterized in that product C is used in a mole ratio of at most 1:100 with product B.

18. A process according to any one of claim 1 characterized in that the reaction is carried out in a closed system, in a semi-open system or in a continuous system, with one or more reaction stages, with agitation and at a temperature of −40° C. to +70° C.

19. A process according to claim 1 characterized in that the propylene is contained in a $C_3$ cut from an oil refining process.

20. A process for selective dimerization of propylene principally into branched dimers comprising dimerizing the propylene in contact with a catalytic composition consisting essentially of at least one nickel compound mixed or complexed with at least one tertiary phosphine carrying a functional group, at least partly dissolved in a non aqueous medium with an ionic nature resulting from bringing at least one aluminum halide (product B) into contact with at least one quaternary ammonium halide and/or at least one quaternary phosphium halide (product A), and optionally a product C, consisting of at least one organometallic aluminum compound.

21. A process for selective dimerization of propylene principally into branched dimers comprising dimerizing the propylene in contact with a catalytic composition consisting of at least one nickel compound mixed or complexed with at least one tertiary phosphine carrying a functional group, at least partly dissolved in a non aqueous medium with an ionic nature resulting from bringing at least one aluminum halide (product B) into contact with at least one quaternary ammonium halide and/or at least one quaternary phosphonium halide (product A), and optionally a product C, consisting of at least one organometallic aluminum compound.

* * * * *

UNITED STATES PATENT AND TRADEMARK OFFICE
CERTIFICATE OF CORRECTION

PATENT NO.    : 6,501,001 B2
DATED         : December 31, 2002
INVENTOR(S)   : Dominique Commereuc et al.

It is certified that error appears in the above-identified patent and that said Letters Patent is hereby corrected as shown below:

Column 7,
Line 33, reads "a funtional group" should read -- a functional group --
Line 37, reads "phosphium halide" should read -- phosphonium halide --
Line 41, reads "and acetylacetonate." should read -- or acetylacetonate --
Line 44, reads "$R^{'1}$" and should read -- $R'_1$ --

Column 10,
Line 4, reads "to any one of claim 1" should read -- to claim 1 --
Line 23, reads "phosphium halide" should read -- phosphonium halide --

Signed and Sealed this

Ninth Day of March, 2004

JON W. DUDAS
*Acting Director of the United States Patent and Trademark Office*